United States Patent [19]

Pontoglio et al.

[11] Patent Number: 4,883,894

[45] Date of Patent: Nov. 28, 1989

[54] PROCESS FOR THE PRODUCTION IN CONTINUOUS OF PHTHALODINITRILE

[75] Inventors: Enrico Pontoglio, Brescia; Sandro Parodi, Nuvolento; Giancarlo Caretti, Brescia, all of Italy

[73] Assignee: Caffaro s.p.a. Societa per l'Industria Chimica ed Elettrochimica, Milan, Italy

[21] Appl. No.: 29,717

[22] Filed: Mar. 24, 1987

[30] Foreign Application Priority Data

Apr. 14, 1986 [IT] Italy .................................. 20077 A/86

[51] Int. Cl.[4] ............................................. C07C 120/00
[52] U.S. Cl. ..................................... 558/311; 558/312; 558/313
[58] Field of Search ......................... 558/311, 312, 313

[56] References Cited

U.S. PATENT DOCUMENTS 2,177,619 10/1939 Nicodemus et al. ................ 558/308
3,070,621 12/1962 Lind .................................... 558/311

OTHER PUBLICATIONS

Chemical Abstracts, vol. 80, No. 22, Abstract: 133,086f, p. 447, Jun. 3, 1974.

Primary Examiner—Mary C. Lee
Assistant Examiner—Zinna N. Davis
Attorney, Agent, or Firm—Wolf, Greenfield & Sacks

[57] ABSTRACT

The present invention relates to a process for the production in continuous of isophthalodinitrile or terephthalodinitrile by simultaneous amidation and dehydration of the respective acid chlorides in steam phase on a fixed bed of a dehydration catalyst.

7 Claims, No Drawings

PROCESS FOR THE PRODUCTION IN CONTINUOUS OF PHTHALODINITRILE

BACKGROUND OF THE INVENTION

1. Field of the Invention

The present invention relates to a process for the production in continuous of phthalodinitrile. More particularly the present invention relates to a process for the production in continuous of isophthalodinitrile or terephthalodinitrile by simultaneous amidation and dehydration of the respective acid chlorides in steam phase on a fixed bed of a dehydration catalyst.

2. Prior Art

Dinitrils of arylic acids can be prepared only by complex chemical methods or adopting sophisticated and expensive equipment. The classical method, from carboxylic acids by reaction with ammonia in steam phase of dehydration catalysts, is not easily applicable due to the chemical-physical characteristics of the starting acids. In fact many solid aromatic acids, such as, for example, phtalic acids, are difficult to vaporize, melt at high temperatures and already at these temperatures they begin to decompose developing carbon dioxide.

Consequently, attempts have been made, to overcome these difficulties in different ways, for example dispersing the pulverized aromatic acid in a stream of inert gas at a temperature below its melting point, mixing it with a very hot ammonia stream and conveying the vaporized reaction products on a dehydration bed. This method, claimed in U.S. Pat. No. 3,070,621, which avoids the melting of the aromatic acid, considerably reduces the decomposition phenomenon and therefore the forming of deposits and crusts on the reactor walls, especially in that zone used as evaporizer. Anyway it is evident that this results in considerable installation difficulties and it is therefore clear why successively other ways were tried, such as for instance the use of phtalic acids derivatives, which vaporize more easily: for example, ammonium salts, diamides and above all esters of such acids, wherein the alkyl chain contains from 1 to 4 carbon atoms. Thus, for example, DTAS No. 1,279,020 claims the preparation of aromatic nitriles from the methyl esters of the correspondent acids: these processes, if on the one hand, simplify the installations, on the other hand raise the new problem of the precursor production, which precursor are not easily available on commercial and industrial scale.

Only in the last 20 years new processes of ammonooxidation were industrially developed, which consist in reacting aromatic hydrocarbon mixtures containing an alkyl chin, oxygen and air, and ammonia at high temperatures on suitable vanadium, tungsten catalysts, etc. However, these processes require high technologies, suited to effect the reactions in steam phase, on fluidized beds; separation and recycle of the unreacted compounds or of the reaction intermedies, use of particular and sophisticated catalysts, and in addition plants of considerably sizes are needed, which require high capital investments.

The Applicant has now surprisingly found a continuous process which allows to obtain isophthalodinitrile and terephthalodinitrile by adopting a simple technology, in plants of reduced costs and dimensions, starting from chlorides of the respective acids; i.e. from cheap row materials, commercially available and/or easily manufactured on industrial scale, and which finally allows a flexible production.

SUMMARY OF THE INVENTION

Therefore it is an object of the present invention a process for the preparation in continuous of compounds of formula (I)

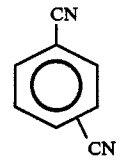
(I)

by reacting a compound of formula (II)

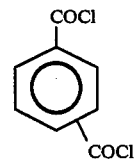
(II)

with ammonia vapours in the presence of a dehydration catalyst, characterized in that:
(a) the compounds of formula (II) are reacted in vapour phase;
(b) the reaction is carried out in absence of solvent;
(c) the catalyst is in form of a fixed bed wherein the temperature ranges from 250° to 450° C.

As already mentioned, the employed row materials which substantially characterized and process, consist of chlorides or pure or technic grade phtalic acids; such chlorides are commercially available since they are the basic products for the production of polyamide and polyester resins and can be easily obtained from the correspondent acids by reaction with thionyl chloride and phosgene etc., or even more economically, by photoclorination of the respective xylene and the subsequent reaction of the resultant α, α,α, α',α', α', hexachloroxylene with the correspondent phtalic acid.

Such acid chlorides are liquid or low melting compounds and are easily to vaporize; therefore taking advantage of these favourable characteristics their vapours pure or preferably diluted in an inert gaseous medium, such as for example air or nitrogen, possibly pre-heated, are slut through a fixed bed, comprising a dehydration catalyst maintained at the desired temperature by means of a suitable outer heating.

Separately and contemporaneously ammonia gas, preferably pre-heated at temperatures very close to the reaction temperatures, is introduced into the bed.

Due to the presence of the catalyst and due to the high temperature, both the amidation and dehydration reactions istantaneously occur.

Therefore steam, phthalodinitrile and ammonium chloride vapours are formed, at last one due to the high temperature, substantially dissociated is hydrocholoric acid and ammonia.

The reaction gases and vapours coming out from the reactor are cooled and in this way a mixture of phtalodinitrile and ammonium chloride is recovered.

In this powder mixture, by an abundant water wash, the nitrile is separated from the ammonium salt and a product of very high purity is obtained, generally with a title ≧99%.

The yields, based upon the acid chloride, are very close to 100%.

In alternative, the reaction gases can be directly and continuously removed by means of water and the resulting suspension can be directly filtered.

The dehydration catalysts suitable to be used are known in the art and have been described in some papers, for example in "Catalysis" by Berkman, Morrel and Egloff. For the considered purposes, some catalysts, such as activated alumina, silica and thorium dioxide (torina), which are stable at the process temperatures, have proved to be particularly satisfactory. Other catalysts include zirconium, beryllium, tungsten and vanadium oxides, basic aluminum phosphaate, basic aluminum sulphate and phosphoric acid; as support for the catalyst alundum can, for example, be used.

As the heat balance of the total reaction is lightly endothermic, it is convenient to maintain the temperature in the catalytic bed at the pre-fixed values, either by direct pre-heating of the reactor and by pre-heating of the inlet gases and vapours.

The molar ratio between ammonia and chloride of the phtalic acid is preferaby maintained equal or lower than the stoichiometric value and therefore any recycle is useless.

The contact times are maintained from 0.1 to 10 seconds, preferably from 1 to 3 seconds.

In the claimed process the reaction has been carried out at atmospheric pressure, but it is possible, even if not necessary, to operate also at superatmospheric or subatmospheric pressures.

A further object of the present invention are the terephtalodinitrile and the isophtalodinitrile obtained by the above mentioned process.

The herein enclosed examples are given to better illustrate the process without however having a limitative character.

EXAMPLE 1

Technic grade isophthaloilchloride (0.0892 M/h) vaporized in a nitrogen stream (1.3299 M/h) is fed at the bottom of a fixed bed reactor, having a 4 cm diameter and a 20 cm lenght, loaded with 90.7 g (about 114 cc.) of activated alumina in form of microspheres having a diameter ranging from 1.5 to 2 mm.

Contemporaneously a mixture of ammonia gas (0.4950 M/h) and nitrogen (3.6801 M/h) is sent to the bottom of the catalyst-layer. The two feed streams are suitably pre-heated, before the mixing, to maintain the catalytic bed, outwardly heated by resistors, in the desired temperature range of 340° ÷ 350° C.

The calculated contact time for these conditions is about 65 seconds;

The gaseous and vapours from the top of the reactor are cooled in a tank vessel at room temperature.

There the isophthalonitrile and the ammonium chloride desublimate as a white and fine crystalline powder, while the escaping gases and vapours ($N_2$, $NH_3$, $H_2O$) are sent to a water spray removing system.

After a reaction period of six hours, the collected solid is abundantly washed with water to remove the ammonium chloride, filtered and finally dried in an oven at 70° C.

In total 66.3 g of product are obtained.

The I.R. and gas-chromatographic analysis confirm that it is isophthalonitrile having a purity degree of 99.8%. The reaction yield, based upon the isophthaloilchloride, is therefore 96.6%.

Similar results are obtained using terephthaoilchloride.

EXAMPLE 2

Using the apparatus and the process of example 1, vapours of isophthaloilchloride (0.2565 M/h), gaseous ammonia (1.2348 M/h) and nitrogen (2.8354 M/h) are fed in continuous for 43 hours and 43' at a reaction temperature of about 350° C.

In this case the volume of the catalytic bed has been increased (about 180 cc) and therefore the relative contact time is about three seconds.

Finally 152.1 g of 99.2% isophtalonitrile, with a 97.4% molecular yield based upon the isophthaloilchloride are collected after the usual purification operations.

Similar results are obtained using terephthaloilchloride.

EXAMPLE 3

With the same modalities, vapours of isophthaloilchloride (0.2526 M/h), gaseous ammonia (0.6350 M/h) and nitrogen (2.8354 M/h) are sent at the bottom of the same previously described reactor.

The reaction temperature (350° C.) and the reactor loading degree ($Al_2O_3$ 180 cc) are maintained as in Example 2.

In this case, the gaseous effluents, escaping from the desublimator are acid due to the presence of the hydrochloric acid and contemporaneously considerably lower quantities of ammonium chloride are produced;

Such differencies are explainable by the fact that the molar ratio between ammonia and isophthaloilchloride (about 2.5) used is such lower than stoichiometric value;

The isophthaloilnitrile, after the usual purification operations, is 188.6 g with a title of 98.9%.

The molar yield is therefore 95%.

Similar results are obtained using terephtaloilchloride.

EXAMPLE 4

Example 1 is repeated with the same modalities but substituting nitrogen by air.

Isophtalonitrile is obtained with a title of 99.5% with a yield of 98%.

Similar results are obtained using the terephthaloilchloride.

We claim:

1. Process for the preparation of a compound of formula (I)

by reacting a compound of formula (II)

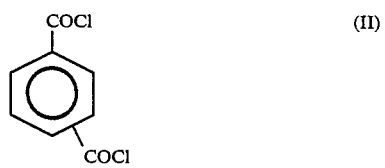

with ammonia vapours in the presence of a dehydration catalyst, wherein the improvement is that
(a) the compounds of formula (II) are reacted in the form of vapours;
(b) the reaction is effected in the absence of solvent;
(c) the catalyst is in the form of a fixed bed, the temperature of which ranges from 250 to 450° C.

2. Process according to claim 1, wherein the ammonia vapours are pre-heated.

3. Process according to claim 1 wherein the compounds of formula (II) are conveyed by a stream of inert gas.

4. Process according to claim 1, wherein ammonia is used in an amount lower than the stoichiometric amount.

5. Process according to claim 1, wherein the compound of formula (I) and any $NH_4Cl$ formed are recovered in an appropriate condenser, then the nitrile is isolated and purified by water washing.

6. Process according to claim 1, wherein the catalytic bed consists of alumina, thorium oxide, aluminum or barium phosphate and silica gel.

7. Process according to claim 1 wherein the catalytic bed consists of alumina, thorium, oxide, aluminum or barium phosphate or silica gel.

* * * * *